(12) United States Patent
Yamazoe et al.

(10) Patent No.: US 10,966,597 B2
(45) Date of Patent: Apr. 6, 2021

(54) FORWARD AND ANGLE VIEW ENDOSCOPE

(71) Applicants: Canon U.S.A., Inc., Melville, NY (US); Kenji Yamazoe, Tochigi (JP); Anderson Mach, Cambridge, MA (US); Zhuo Wang, Santa Clara, CA (US)

(72) Inventors: Kenji Yamazoe, Tochigi (JP); Anderson Mach, Cambridge, MA (US); Zhuo Wang, Santa Clara, CA (US)

(73) Assignee: Canon U.S.A., Inc., Melville, NY (US)

( * ) Notice: Subject to any disclaimer, the term of this patent is extended or adjusted under 35 U.S.C. 154(b) by 383 days.

(21) Appl. No.: 15/750,326

(22) PCT Filed: Aug. 4, 2016

(86) PCT No.: PCT/US2016/045572
§ 371 (c)(1),
(2) Date: Feb. 5, 2018

(87) PCT Pub. No.: WO2017/024145
PCT Pub. Date: Feb. 9, 2017

(65) Prior Publication Data
US 2018/0214008 A1    Aug. 2, 2018

Related U.S. Application Data

(60) Provisional application No. 62/201,251, filed on Aug. 5, 2015.

(51) Int. Cl.
*A61B 1/00* (2006.01)
*A61B 5/00* (2006.01)
(Continued)

(52) U.S. Cl.
CPC ...... *A61B 1/00181* (2013.01); *A61B 1/00096* (2013.01); *A61B 1/00165* (2013.01);
(Continued)

(58) Field of Classification Search
CPC ............ A61B 1/00181; A61B 1/00096; A61B 1/00165; A61B 1/00172; A61B 1/00177; A61B 1/00179
See application file for complete search history.

(56) References Cited

U.S. PATENT DOCUMENTS 3,976,360 A    8/1976 Schroder
4,074,306 A    2/1978 Kakinuma et al.
(Continued)

FOREIGN PATENT DOCUMENTS

JP    2001099617 A    4/2001
WO    9321548 A1    10/1993
(Continued)

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.
(Continued)

*Primary Examiner* — Timothy J Neal
*Assistant Examiner* — Jae Woo
(74) *Attorney, Agent, or Firm* — Canon U.S.A., Inc. IP Division

(57) ABSTRACT

Exemplary apparatus and optical systems for forward and side view apparatus are described. These apparatus include a light focusing element, a grating element inclined with respect to the optical axis of the apparatus, and a transparent element. The transparent element has a proximal surface in contact with the grating element and an inclined distal surface. Such apparatus can be used as spectrally encoded endoscopy (SEE) probes.

16 Claims, 5 Drawing Sheets

(51) Int. Cl.
*A61B 1/07* (2006.01)
*G02B 23/24* (2006.01)

(52) U.S. Cl.
CPC ...... *A61B 1/00172* (2013.01); *A61B 1/00177* (2013.01); *A61B 1/00179* (2013.01); *A61B 1/00188* (2013.01); *A61B 5/0062* (2013.01); *A61B 5/0084* (2013.01); *G02B 23/2461* (2013.01); *A61B 1/07* (2013.01)

(56) References Cited

U.S. PATENT DOCUMENTS

| | | | |
|---|---|---|---|
| 4,264,127 A | | 4/1981 | Schumacher et al. |
| 5,279,280 A | | 1/1994 | Bacich et al. |
| 5,565,983 A | | 10/1996 | Barnard |
| 5,625,499 A | * | 4/1997 | Chen .................. G02B 5/04 359/569 |
| 5,909,529 A | | 6/1999 | Bhagavatula |
| 6,282,034 B1 | | 8/2001 | Onishi et al. |
| 6,341,036 B1 | | 1/2002 | Tearney et al. |
| 6,485,413 B1 | | 11/2002 | Boppart et al. |
| 6,661,513 B1 | | 12/2003 | Granger |
| 6,831,781 B2 | | 12/2004 | Tearney et al. |
| 6,858,859 B2 | | 2/2005 | Kusunose |
| 6,965,475 B2 | | 11/2005 | Shiozaki et al. |
| 7,003,196 B2 | | 2/2006 | Ghiron |
| 7,342,659 B2 | | 3/2008 | Horn et al. |
| 7,448,995 B2 | | 11/2008 | Wiklof et al. |
| 7,796,270 B2 | | 9/2010 | Yelin et al. |
| 7,843,572 B2 | | 11/2010 | Tearney et al. |
| 7,859,679 B2 | | 12/2010 | Bouma et al. |
| 8,045,177 B2 | | 10/2011 | Tearney et al. |
| 8,064,138 B2 | | 11/2011 | Taira et al. |
| 8,145,018 B2 | | 3/2012 | Shishkov et al. |
| 8,203,708 B2 | | 6/2012 | Lee et al. |
| 8,289,522 B2 | | 10/2012 | Tearney et al. |
| 8,780,176 B2 | | 7/2014 | Yelin |
| 8,804,133 B2 | | 8/2014 | Yelin et al. |
| 8,812,087 B2 | | 8/2014 | Yelin et al. |
| 8,818,149 B2 | | 8/2014 | Shishkov et al. |
| 8,838,213 B2 | | 9/2014 | Tearney et al. |
| 9,057,594 B2 | | 6/2015 | Kang et al. |
| 9,254,089 B2 | * | 2/2016 | Tearney ............ A61B 5/0062 |
| 9,295,391 B1 | * | 3/2016 | Tearney ........... G02B 21/0064 |
| 9,439,568 B2 | * | 9/2016 | Atiya .................. A61B 1/247 |
| 10,321,810 B2 | * | 6/2019 | Ikuta .................. A61B 5/0075 |
| 2002/0008921 A1 | * | 1/2002 | Ebizuka .................. G02B 5/04 359/837 |
| 2002/0114566 A1 | | 8/2002 | Fairchild et al. |
| 2002/0122246 A1 | * | 9/2002 | Tearney ............ A61B 1/00096 359/368 |
| 2002/0145815 A1 | | 10/2002 | Moriyama et al. |
| 2003/0007201 A1 | * | 1/2003 | Dickson .............. G02B 5/1814 359/15 |
| 2003/0027328 A1 | | 2/2003 | Cunningham et al. |
| 2003/0142934 A1 | | 7/2003 | Pan et al. |
| 2004/0070853 A1 | * | 4/2004 | Ebizuka ................. G01J 3/12 359/833 |
| 2004/0076390 A1 | * | 4/2004 | Dong Yang ........ A61B 1/00096 385/116 |
| 2004/0147810 A1 | | 7/2004 | Mizuno |
| 2004/0174529 A1 | | 9/2004 | Maznev et al. |
| 2005/0155704 A1 | | 7/2005 | Yokajty et al. |
| 2006/0182391 A1 | * | 8/2006 | Cifelli .................. G02B 5/32 385/37 |
| 2006/0274391 A1 | * | 12/2006 | Dickson .............. G02B 5/1814 359/1 |
| 2007/0188855 A1 | * | 8/2007 | Shishkov ............ A61B 5/0062 359/362 |
| 2007/0233396 A1 | | 10/2007 | Tearney et al. |
| 2007/0276187 A1 | | 11/2007 | Wiklof et al. |
| 2008/0013960 A1 | | 1/2008 | Tearney et al. |
| 2008/0097225 A1 | | 4/2008 | Tearney et al. |
| 2008/0177138 A1 | * | 7/2008 | Courtney ........... A61B 1/00183 600/109 |
| 2009/0034077 A1 | * | 2/2009 | Kane ..................... G01J 3/12 359/566 |
| 2009/0141360 A1 | | 6/2009 | Koyama |
| 2009/0153932 A1 | | 6/2009 | Davis et al. |
| 2010/0210937 A1 | | 8/2010 | Tearney et al. |
| 2010/0232675 A1 | * | 9/2010 | Ortyn .................. G01N 15/147 382/134 |
| 2011/0237892 A1 | | 9/2011 | Tearney et al. |
| 2011/0275899 A1 | | 11/2011 | Tearney et al. |
| 2012/0057149 A1 | * | 3/2012 | Ohzawa ............... A61B 5/064 356/51 |
| 2012/0112094 A1 | | 5/2012 | Kao et al. |
| 2012/0212595 A1 | | 8/2012 | Parmar et al. |
| 2013/0012771 A1 | | 1/2013 | Robertson |
| 2013/0331709 A1 | | 12/2013 | Le et al. |
| 2014/0153864 A1 | | 6/2014 | Sinclair et al. |
| 2014/0186038 A1 | * | 7/2014 | Frisken ................. G02B 6/356 398/50 |
| 2014/0221747 A1 | | 8/2014 | Tearney et al. |
| 2014/0285878 A1 | | 9/2014 | Escuti et al. |
| 2014/0313315 A1 | * | 10/2014 | Shoham ............... G02B 21/002 348/80 |
| 2014/0378846 A1 | | 12/2014 | Hosoda et al. |
| 2015/0009508 A1 | * | 1/2015 | Bachmann ............ H01S 3/0812 356/479 |
| 2015/0045622 A1 | | 2/2015 | Shishkov et al. |
| 2015/0131098 A1 | | 5/2015 | Yang et al. |
| 2015/0168250 A1 | * | 6/2015 | Saxer ................. G01M 11/0207 356/456 |
| 2015/0335248 A1 | | 11/2015 | Huang et al. |
| 2016/0220104 A1 | * | 8/2016 | Bauer .................. A61B 1/0646 |
| 2016/0265747 A1 | * | 9/2016 | Nagao ................ A61B 1/00096 |
| 2016/0341951 A1 | | 11/2016 | Tearney et al. |
| 2016/0374562 A1 | * | 12/2016 | Vertikov .............. A61B 5/1076 600/424 |
| 2017/0035281 A1 | * | 2/2017 | Takeuchi .............. G02B 23/26 |
| 2017/0176736 A1 | | 6/2017 | Yamamoto et al. |
| 2017/0322079 A1 | * | 11/2017 | Do .......................... G01J 3/0218 |
| 2017/0354317 A1 | * | 12/2017 | Ikuta .................... A61B 5/0075 |
| 2018/0017806 A1 | * | 1/2018 | Wang .................... G02B 27/425 |
| 2018/0084981 A1 | * | 3/2018 | Wang .................. A61B 1/00172 |
| 2018/0120555 A1 | * | 5/2018 | Ikuta .................. G02B 23/2469 |
| 2018/0214008 A1 | * | 8/2018 | Yamazoe ............. G02B 23/2461 |

FOREIGN PATENT DOCUMENTS

| | | |
|---|---|---|
| WO | 2007/084903 A1 | 7/2007 |
| WO | 2013064843 A1 | 5/2013 |
| WO | 2013138656 A1 | 9/2013 |
| WO | 2014031748 A1 | 2/2014 |
| WO | 2014104405 A1 | 7/2014 |
| WO | 2015/042093 A1 | 3/2015 |
| WO | 2015/116951 A2 | 8/2015 |
| WO | 2015116939 A1 | 8/2015 |
| WO | 2015116974 A1 | 8/2015 |
| WO | 2017/024145 A1 | 2/2017 |
| WO | 2017/106347 A1 | 6/2017 |
| WO | 2017/117203 A1 | 7/2017 |
| WO | 2017/139657 A1 | 8/2017 |
| WO | 2017/218496 A1 | 12/2017 |

OTHER PUBLICATIONS

Pitris, C. et al., ("A GRISM-based probe for spectrally encoded confocal microscopy" Optics Express, Jan. 27, 2003, pp. 120-124, vol. 11, No. 2.

Yelin, D., et al., " Three-dimensional miniature endoscopy", Nature, Oct. 19, 2006, p. 765, vol. 443.

Kang, D., et al., "Minature grating for spectrally-encoded endoscopy", Lab Chip, 2013, pp. 1810-1816, vol. 13, No. 9.

Kang, D., et al., "Spectrally-encoded color imaging", Optics Express, Aug. 17, 2009, pp. 15239-15247, vol. 17, No. 17.

(56) References Cited

OTHER PUBLICATIONS

Moharam, M.G., et al, "Formlation for stable and efficient implementation of the rigorous coupled-wave analysis of binary gratings", J. Opt. Soc. Am. A, May 1995, pp. 1068-1076, vol. 12, No. 5.

Yun, et al., "High-speed spectral-domain optical coherence tomography at 1.3 µm wavelength", Opt Express, Dec. 29, 2003, pp. 3598-3604, No. 11, vol. 26.

Tearney, G.J., et al., "Spectrally encoded miniature endoscopy", Optics Letters, Mar. 15, 2002, pp. 412-414, vol. 27, No. 6.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

Barlev, O., et al., "Design and experimental investigation of highly efficient resonance-domain diffraction gratings in the visible spectral region", Applied Optics, Dec. 1, 2012, pp. 8074-8080, vol. 51, No. 34.

\* cited by examiner

FORWARD AND ANGLE VIEW ENDOSCOPE

CROSS-REFERENCE TO RELATED APPLICATION(S)

This application claims priority to U.S. Provisional Application Ser. No. 62/201,251 filed 5 Aug. 2015, the content of which is incorporated herein by reference in its entirety.

FIELD OF THE DISCLOSURE

The present disclosure relates to optical probes. More particularly, the disclosure exemplifies optical probes for endoscopy such as spectrally-encoded endoscopy.

BACKGROUND INFORMATION

Endoscopes are used to view the interior passageway of an object. Endoscopes are used for both medical and technical applications to view confined space where the available pathways for probe advancement are limited, such as in small vessels, joints, organs, small needles, cracks etc.). Conventional miniature endoscopes are generally composed of fiber-optic imaging bundles and an optical system.

To enhance the ability to miniaturize the endoscope, a spectrally encoded endoscope ("SEE") has been developed. U.S. Pat. No. 8,145,018 describes SEE techniques and arrangements which facilitate the use of a single optical fiber to transmit one-dimensional (e.g., line) image by spectrally encoding one spatial axis. (See also, for example, U.S. Pat. No. 7,796,270; U.S. Pat. No. 7,859,679; U.S. Pat. No. 8,045,177; U.S. Pat. No. 8,812,087; U.S. Pat. No. 8,780,176.) By mechanically scanning this image line in the direction perpendicular thereto, a two dimensional image of the scanned plane can be obtained outside of the probe. This technology provides a possibility for designing the probes that are of slightly bigger diameter than an optical fiber. Probes in approximately 100 μm diameter range may be developed using such SEE technology. SEE techniques and systems facilitate a simultaneous detection of most or all points along a one-dimensional line of the image. Encoding the spatial information on the sample can be accomplished by using a broad spectral bandwidth light source as the input to a single optical fiber endoscope.

Spectrally-encoded endoscopy utilizes the ability of the diffraction grating that deflects incident light to a diffraction angle according to wavelength. When the deflected light hit the object, it is scattered by the object. Detecting the scattered light intensity at each wavelength is equivalent to detecting the intensity from the diffraction angle. Thus, one-dimensional image of the object is obtained. However, as the grating deflects the light, the incident light is usually bent with respect to the optical axis. In this way, no light goes straight with respect to the optical axis. As no light goes straight, it is not capable with conventional spectrally-encoded endoscopy configuration to view forward direction.

Current trend of the spectrally-encoded endoscopy employs side-view type, with a few examples exhibiting forward viewing characteristics. The front-view type consists of multiple components—prism and grating, making the probe design complicated. Examples of such designs can be found, for example, in C. Pitris et al., (B. E. Bouma, M. Shiskov, G. J. Tearney, OPTICS EXPRESS Vol. 11 120-124 (2003) and U.S. Pat. No. 8,145,018, both of which discloses a dual prism configuration where a grating is sandwiched between two prisms (a "grism"). This grism directs spectrally dispersed light in the directions including the optical axis of the fiber. The grism consists of multiple components (grating, prisms) which will need proper alignment. The need of a grism will increase the cost, complexity of fabrication and size of the probe.

Thus, there is a need to provide forward view SEE with an endoscope that has a lower cost and/or complexity compared to prior apparatus.

SUMMARY OF EXEMPLARY EMBODIMENTS

According to at least one embodiment of the invention, there is provided an apparatus comprising optics where the grating is angled with respect to the optical axis of the apparatus and the grating is not exposed to the outside of the probe.

In some embodiments, the apparatus comprises a light focusing element, a grating element is inclined with respect to the optical axis, and a transparent element having a proximal surface in contact with the grating element and a distal surface that is angled with respect to the optical axis of the apparatus. When light passes through the light focusing element, it is incident on the grating and, after diffracting from the grating, the light is refracted by the distal surface of the transparent element. A spacer element may be located between the light focusing element and the grating element. Preferably, the refractive index of the spacer element, $\eta_1$, is less than the refractive index of the transparent element, $\eta_2$. Preferably, the grating and transparent elements are formed as a single molded component.

In some embodiments, the apparatus also includes a sheath element covering at least a portion of the apparatus.

Other embodiments also provide an endoscope that comprises the apparatus as described herein. The endoscope may be a side-view endoscope where the distal surface of the transparent element is included at an angle, $\beta$, from 40° to 110°, from the optical axis of the endoscope and a grating angle $\alpha$, from 40° to 80° from the optical axis of the endoscope. The relationship between $\alpha$ (or $\theta$, which is 90−$\alpha$) and $\beta$ is defined according to equations 1-8 below. The side-view endoscope may provide, for example, spectrally dispersed light having a range of angles between 30° to 90° with respect to the optical axis of the endoscope.

The endoscope may be a forward-view endoscope where the distal surface of the transparent element is included at an angle, $\beta$, from 50° to 70°, from the optical axis of the endoscope and a grating angle $\alpha$, from 40° to 80° from the optical axis of the endoscope. The forward-view endoscope may provide, for example, spectrally dispersed light having a range of angles between −10° to 10° with respect to the optical axis of the endoscope.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 7(a), 7(c), 7(e), and 7(g) are blue rays. FIGS. 7(b), 7(d), 7(f), and 7(h) are red rays. The refractive index of the prism, $n_2$ is 1.7 (FIGS. 7(a) and 7(b)), 1.6 (FIGS. 7(c) and 7(d)), 1.5 (FIGS. 7(e) and 7(f)), and 1.4 (FIGS. 7(g) and 7(h)).

Figure 1A:
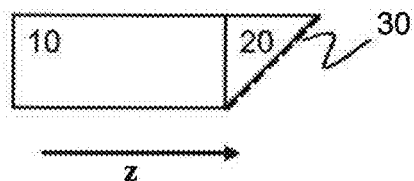
FIG. 1(a) is a simplified probe design.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The embodiments are based on the object of providing an apparatus for spectrally encoded endoscopy ("SEE") that allows for either forward viewing or side viewing endoscopy. With the probe as described herein, diffracted light can be sent parallel to the axis of the GRIN lens, enabling the front-view SEE probe. The light can be diffracted by a single molded component easing manufacturability. One advantageous feature of embodiments of this invention is that the grating—a delicate component, is not exposed to the outside of the probe.

Figure 1B:
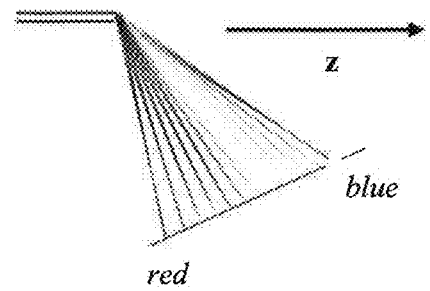
FIG. 1(b) is a ray-tracing example if the spectrally encoded probe of FIG. 1(a).

The conventional SEE probe is briefly explained and shown in FIG. 1A. In FIG. 1A, the light focusing element 10 such as a GRIN lens focuses light through a transparent (or transmissive) element 20 onto a grating 30. FIG. 1(b) is a ray tracing to show how the configuration of FIG. 1(a) works. In FIG. 1(b), light is guided by a fiber to the element 10. Note that the incident light is deflected according to the wavelength. In addition, no light goes straight (z-direction) in FIG. 1(b).

Forward View Embodiments

Figure 2A:
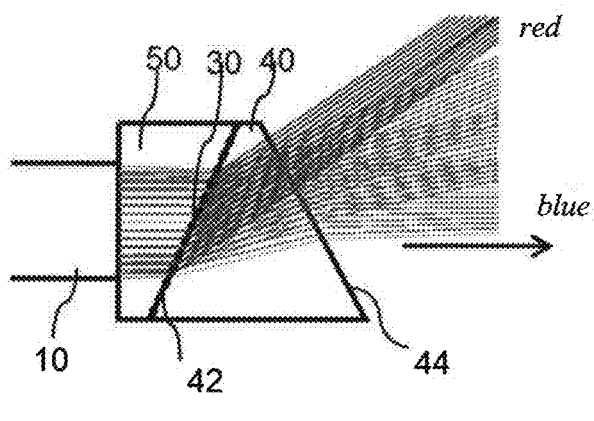
FIGS. 2(a) and 2(b) show an exemplary front-view SEE probe with two different perspectives.

An exemplary forward-view embodiment is depicted by FIG. 2(a). This embodiment provides an apparatus that uses a single component that includes both the grating 30 and transparent element 40 to realize spectrally dispersed light to be directed toward the optical axis of the fiber (shown as an arrow in FIG. 2(a)). The transparent element has two angled surfaces, 42 and 44. The schematic view of FIG. 2(a) shows a light focusing element to such as a GRIN lens focusing light through a spacer element 50 such as an air gap or an epoxy spacer onto a grating 30 that is found at an incline with respect to the optical axis of the apparatus (which is also the GRIN lens optical axis). The grating 30 is in contact with the proximal surface 42 of a transparent element 40, shown in FIG. 2(a) as a prism. In some embodiments, the grating 30 is formed or transferred onto this proximal surface 42. Light passes through the grating 30 and is diffracted. It then passes through the transparent element 40 and is refracted at the distal surface 44 of the transparent element 40 which is also at an inclined angle with respect to the optical axis. In some embodiments, the angle of the proximal surface 42 and the distal surface are different. In some embodiments, the transparent element 40 can have multiple faceted angles. In some embodiments, the transparent element has at least one surface that has a mirror polish.

Figure 2B:
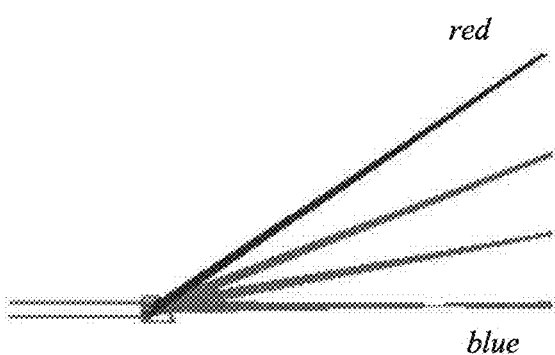

In this embodiment, which can be seen in both FIG. 2(a) and in the expanded FIG. 2(b) blue light is propagated substantially parallel to the optical axis of the apparatus and red light is refracted off-axis to provide a spectral line that is particularly useful as a SEE probe. Here, the refractive index of the grating is assumed to be 1.60 (no dispersion) and the refractive index of the GRIN lens is assumed to be $n(r)=1.610-0.1504r^2$, where r is the radial distance from the center of the GRIN lens.

In this embodiment, the light comes through a GRIN lens 10 through a spacer element 50 which is an air gap. The GRIN lens, a Go!Foton lens SRL 035 is a 3.9 mm lens (0.2617 pitch). The light is then incident on grating 30 which as a grating itch of 820 nm. The light then diffracts through a prism 40 (shown as a polycarbonate Lexan HPH4404 prism with a refractive index of 1.58) which has a proximal angle of α=65° (this is also described as the grating angle) and a distal angle of β=60° (also described as the prism angle).

The light focusing element 10 can be a gradient index lens (GRIN) lens or other light focusing lenses or other light focusing elements. Exemplary GRIN lenses are those manufactured and sold by, for example Toyo or Go!Foton. Light incident on the light focusing element may be provided by a waveguide, such as an optical fiber. This fiber may, for example, be splice or otherwise attached to the light focusing element either concentrically or where the waveguide is off-centered compared to the light focusing element axis. The off-centered waveguide will provide light emitting through the focusing element 10 that is offset from the axis of the light focusing element 10. The apparatus may include a data generation element configured to receive and process light received from the apparatus.

The spacer element 50 is optionally located between the GRIN lens and an excitation fiber. A spacer is particularly useful in providing a different refractive index between the spacer element 50 and the transparent element 40 and thus providing high diffraction efficiency. In some embodiments, an air gap used as the spacer element 50 provides a sufficient difference in refractive index. However, in some embodiments, a material having a lower refractive index is used. These embodiments have a particular advantage in that the transparent element 40 can be supported mechanically by the spacer element 50 and no additional structures are needed to connect the transparent element 40 to the focusing element 10. In these embodiments, the diameter of the whole probe may be able to be smaller as well. With an air gap used as the spacer element, 50 some preferred embodiments include a sheath that connects the transparent element 40 to the focusing element 10. In one exemplary embodiment, a Go!Foton SRL 035 lens and a spacer together can have a distance of 3.9 mm and the 0.2617 pitch is retained.

The Lexan prism 40 of this embodiment has a grating pitch of 820 nm which gives a 65° angle for the surface on which the grating is placed and a 60° angle for light exiting the prism. Thinner spacers can be used to make the diameter smaller.

Fabrication of the grating element may be accomplished in several ways. The single optical component that forms the grating 30 and transparent element 40 may be made of either plastic or glass. In some embodiments, the transparent element 40 is made via injection molding. In some embodiments, where the spacer element 50 is not air, the transparent element 40 may be molded first tighter with grating surface 30 and then the spacer element 50 is formed by injection molding in a co-molding process.

In some embodiments, the grating may be stamped using a transparent element body of glass or plastic on the face of the transparent element. In other embodiments, a grating of polymer material will be injection molded with the plastic transparent element and grating combined as a single component. In other embodiments, a grating of glass material will be fabricated by directly etching the grating onto the glass transparent element or the spacer element. The glass will then be cut to dimensions of the transparent element.

The apparatus as disclosed herein may be fabricated with, for example, either a stamped or plastic grating component. The components for one exemplary fabrication include: a plastic transparent element including a grating; a light focusing element such as a GRIN lens, a ball lens, etc.; a sheath made from, for example, plastic, metal, heatshrink, or glass; an air gap spacer, and epoxy. In this embodiment, the focusing element will be fixed within the sheath with epoxy. An air gap spacer with a thru hole will then be epoxied at the distal end of the focusing element. Next the transparent element with grating will be epoxied on the other end of the air gap spacer in the sheath. Finally, with all the components of the probe tip fixed, the distal surface of the transparent element with grating tip can be polished at a desired angle for 'forward' or 'side' viewing.

In another embodiment, an exemplary fabrication of an apparatus as disclosed herein having a glass grating component is provided. The components for this exemplary fabrication include: a glass transparent element including a grating; a light focusing element such as a GRIN lens, a ball lens, etc.; a sheath made from, for example, glass; an air gap spacer, and epoxy. In this embodiment, high heat processing may be used to assemble the components. With a fusion splicer, a glass sheath will be tapered onto the glass transparent element with grating fixing it within the sheath. Then, translation stages will be used to align the focusing element within the other end of the sheath at a set distance from the grating. For ball lens or high Tg optics (e.g., Silica GRIN), the fusion splicer will taper the full sheath fixing both the focusing element and the glass transparent element. Alternatively, for Low Tg optics, the focusing element will be epoxied to the inner wall of the sheath. With all the components of the probe tip fixed, the distal surface of the transparent element with grating tip can be polished at a desired angle for 'forward' or 'side' viewing.

Side View Embodiment

Figure 3A:
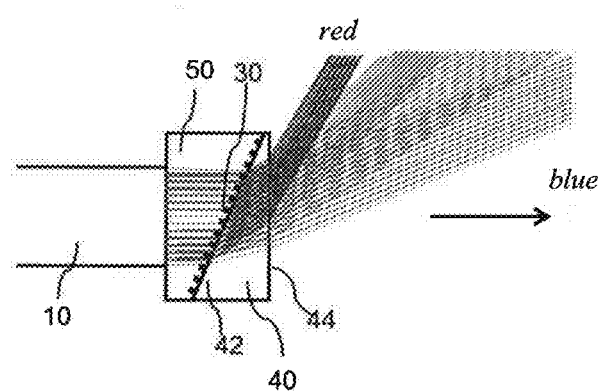
FIGS. 3(a) and 3(b) show an exemplary angled side-view SEE probe with two different perspectives.

Depending on the angle of the distal surface 44, as well as the proximal surface 42, the emitted light can be used for 'Front-view' (FIG. 2) or alternatively angled to provide 'Side-view' (discussed below as FIG. 3). In the embodiment described by FIG. 3, the light propagates similar to that as shown in FIG. 2. This embodiment provides an apparatus that uses a single component that includes both the grating 30 and transparent element 40 to realize spectrally dispersed light to be directed toward the optical axis of the fiber (shown as an arrow in FIG. 3(a)). The transparent element has two angled surfaces, 42 and 44. The schematic view of FIG. 3(a) shows a light focusing element 10 such as a GRIN lens focusing light through a spacer element 50 such as an air gap or an epoxy spacer onto a grating 30 that is found at an incline with respect to the optical axis of the apparatus (which is also the GRIN lens optical axis). The grating 30 is located on the proximal surface 42 of a transparent element 40, shown in FIG. 2(a) as a right angled optical element. Light passes through the grating 30 and is diffracted. It then passes through the transparent element 40 and is refracted at the distal surface 44 of the transparent element 40 which is also at an inclined angle with respect to the optical axis. In some embodiments, the angle of the proximal surface 42 and the distal surface are different.

Figure 3B:
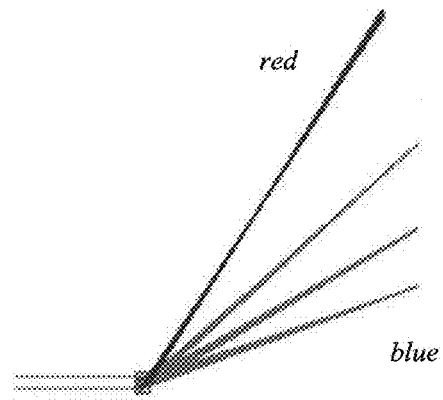

In this side view embodiment, which can be seen in both FIG. 3(a) and in the expanded FIG. 3(b) blue light is propagated at an angle compared to the optical axis of the apparatus and red light is propagated at close to perpendicular to the optical axis, providing a side view of a sample surface on which the spectrum of light impinges. This configuration is useful as a SEE probe. As in the prior embodiment, the refractive index of the grating is assumed to be 1.60 (no dispersion) and the refractive index of the GRIN lens is assumed to be $n(r)=1.610-0.1504r^2$, where r is the radial distance from the center of the GRIN lens.

In some embodiments, the spacer element 50 is preferably thin compared to the thickness of the transparent element. Since light exiting the focusing element 10 is close to be collimated, the thickness of the spacer is not very critical for optical alignment. A thinner spacer will be advantageous to form a more flexible probe since the portion of the probe housing the focusing element 10 and the transparent element 40 will be more rigid.

Figure 4:
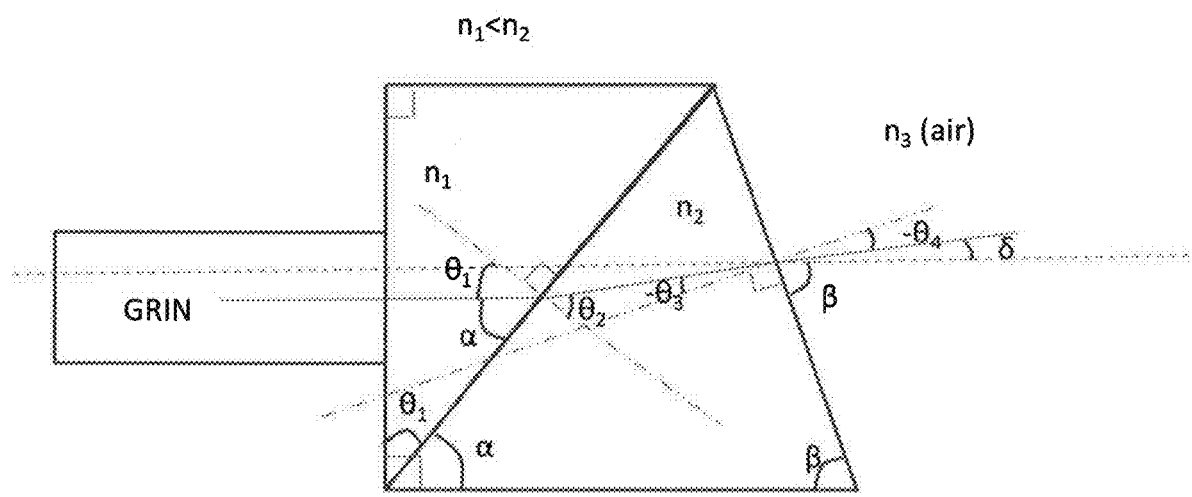
FIG. 4 is a schematic view of an embodiment of the inverse grating design.

FIG. 4 shows the schematic for the inverse grating design. The collimated light (in red) after the GRIN lens or ball lens will enter a medium with a refractive index $n_1$ before it hits the grating which is on one side of a triangular prism of a refractive index $n_2$. The light then exits from another side of the triangular prism into a medium with a refractive index $n_3$. Here we define a triangular prism as a three-sided prism, i.e. it is a polyhedron made of a triangular base, a translated copy, and 3 faces joining corresponding sides. For the designs described afterwards, it is required that $n_1<n_2$. This condition is usually satisfied if the GRIN lens is separated with the triangular prism by an air gap, i.e. $n_1=1$. It is also possible to have a lower refractive index material (e.g. epoxy or silicone) as the spacer between the GRIN lens and the prism so that the GRIN lens and the prism are connected into one piece without the need for extra holders.

Here we assume the light incident angle on the grating surface is $\theta_1$. The light exit angle is thus $\theta_2$ as shown in FIG. 4. The sign convention is defined such that clockwise is positive as the incident light rotates to the surface normal. As a result of this convention, the light incident angle to the second surface of the triangular prism shown in FIG. 1 is thus $-\theta_3$ and the corresponding light exit angle is $-\theta_4$. We are particularly interested in the angle between the exit ray and the rotational axis of the GRIN lens (or ball lens). This angle is defined as $\delta$ as shown in FIG. 4.

Design

Figure 5:
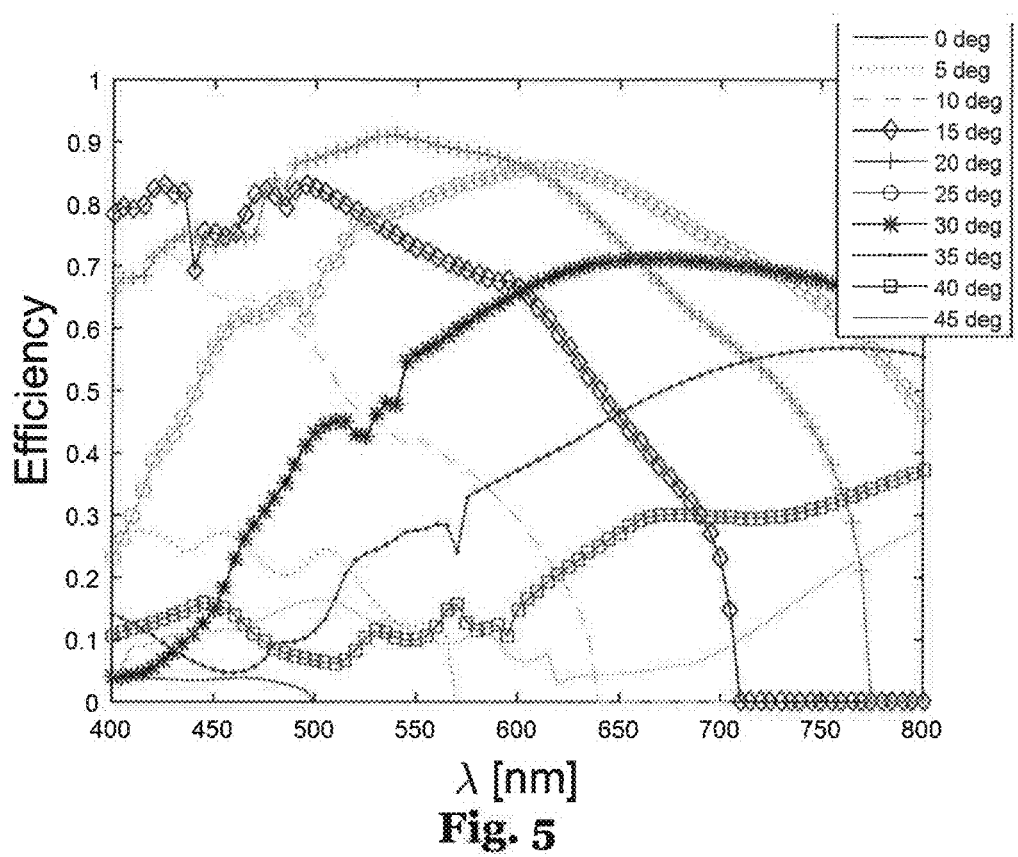
FIG. 5 is a chart showing an exemplary averaged grating efficiency vs. wavelength at different light incident angles.

The averaged grating efficiency varies greatly with wavelength and also varies as the incident angle is varied. Thus, as shown in FIG. 5, in order to maximize efficiency, both the incident angle and the wavelength must be taken into account.

According to the geometry, it is obvious that the following condition holds:

$$\left(\frac{\pi}{2} - \theta_1\right) + \left(\frac{\pi}{2} + \theta_2\right) + \left(\frac{\pi}{2} - \theta_3\right) + \beta = 2\pi. \quad (1)$$

As a result of Eq. 1, we have $$\theta_3 = -\frac{\pi}{2} - \theta_1 + \theta_2 + \beta. \quad (2)$$

Similarly, the following relationship can be derived based on the geometry:

$$\delta = \frac{\pi}{2} - \beta + \theta_4. \quad (3)$$

Base on Eq. 3, it is obvious that $$\theta_4 = -\frac{\pi}{2} + \beta + \delta. \quad (4)$$

The angles $\theta_1$ and $\theta_2$ are connected via the grating equation, $$-n_1 \sin \theta_1 + n_2 \sin \theta_2 = mG\lambda, \quad (5)$$

where m is the diffraction order, G is the grating spatial frequency (unit: $1/\mu m$) and $\lambda$ is the wavelength of the light (unit: $\mu m$).

By solving Eq. 5, the exit angle $\theta_2$ is thus $$\theta_2 = \arcsin[(mG\lambda + n_1 \sin \theta_1)/n_2] \quad (6)$$

Similarly, the angles $\theta_3$ and $\theta_4$ are governed by the Snell's law as $$n_2 \sin(-\theta_3) = n_3 \sin(-\theta_4), \quad (7)$$

where $n_3$ is the refractive index of the surrounding area, which is usually air (i.e. $n_3=1$) for our application.

Combining Eqs. 2, 4 and 7, we are able to derive the tilt angle $\delta$ as a function of the incident angle $\theta_1$ and prism angle $\beta$ as $$\delta = \arccos[n_2 \cos(-\theta_1 + \theta_2 + \beta)/n_3] - \beta, \quad (8)$$

where $\theta_2$ is decided by Eq. 6.

According to Eq. 8, in order to achieve different viewing angles for the probe (i.e. forward view or side view), we can vary the incident angle $\theta_1$ or the prism angle $\beta$ or both. It is also possible to change the grating related parameters such as the refractive indexes $n_1$ and $n_2$, diffraction order m and the grating frequency G. However, it is worth noting that the incident angle $\theta_1$ is often times decided by the grating design to achieve a higher optical efficiency. A larger incident angle $\theta_3$ will introduce higher Fresnel loss and thus decrease the efficiency. For some extreme cases, $\theta_3$ may exceed the critical angle and result total internal reflection (TIR), i.e. no light can exit from the prism. TIR is not desired for our current application. However, it is the working condition for some special applications such as TIR fluorescence or TIR endoscopic/microscopic imaging.

Exemplary Case Studies

Figure 6:
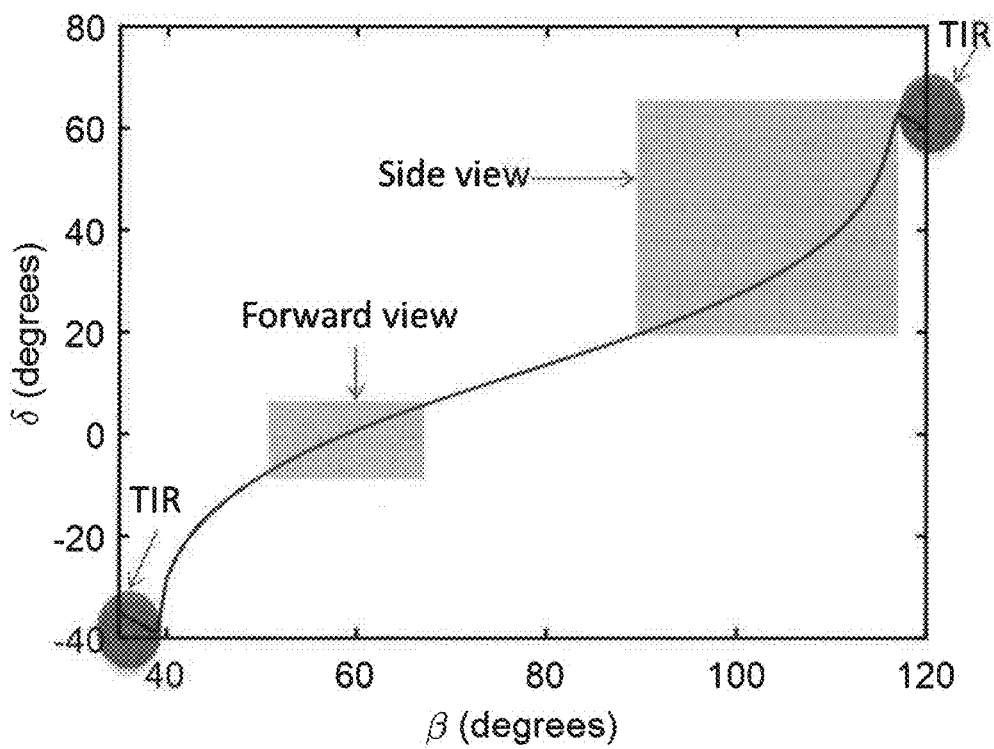
FIG. 6 is a diagram for an exemplary embodiment where the exit angle δ is plotted versus prism angle β. The regions for forward and side view are indicated as well as the regions where total internal reflection (TIR) occurs.

Here we first study the relationship of the blue ray exit angle $\delta$ as a function of the prism angle $\beta$. We assume $n_1=n_3=1$ (air), grating frequency $G=1/0.82 \mu m^{-1}$, $\lambda=0.45 \mu m$ and the diffraction order $m=1$. For this specific design, the light incidence angle on the grating is fixed at 25.4° in order to maximize the diffraction efficiency at all wavelengths. FIG. 6 shows the current grating design we have in house. At 25.4° incident angle, we can achieve higher than 50% diffraction efficiencies for the wavelengths ranging from 450 nm to 780 nm.

Based on the aforementioned parameters and Eq. 8, the deflection angle vs. prism angle is plotted in FIG. 6. For the design shown here, the angle $\delta$ is close to 0° when $\beta=60°$ and close to 20° when $\beta=90°$. If we define a forward view probe as the lowest viewing angle to cover at least the range of +5°/−10°, by controlling the angle $\beta$ in the vicinity of 60° (shown in FIG. 6 as the rectangular shaded area) it is possible to get a forward view probe. If we define a side view probe such that the lowest viewing angle to be larger than 20°, the probe will thus become side view if $\beta$ is larger than 90° (shown in FIG. 6 as the rectangular shaded area). For positive diffraction orders, the lowest viewing angle is decided by the diffraction angle of the blue ray. Two round shaded areas in FIG. 6 show when the $\beta$ angle is either too small or too large, TIR will happen which makes the probe unusable.

We further studied the relationship between the light incident angle on the grating $\theta$ (here for convenience we define $\theta=\theta_1$) and the light deflection angle $\delta$ with respect to different prism angles $\beta$ as shown in FIGS. 7(a)-7(h). Here we assume the refractive index of the prism ($n_2$) to be 1.6. Many plastic materials including all kinds of polycarbonate, PET, etc. have a refractive index number close to 1.6. A lot of glass materials can also have similar refractive indexes. The shaded rectangular areas highlight the usable ranges for both forward view and side view probe designs. Once the incident angle $\theta$ is fixed, e.g. $\theta=20°$, the corresponding ranges for the prism angle $\beta$ is determined for both forward view probes ($\beta\sim55°$) and side view probes ($\beta>85°$).

Similarly, according to Eq. 8 we can study the red ray exit angle $\delta$ as a function of the prism angle $\beta$ and the grating angle $\theta$. One may notice the highest angle $\beta$ goes to 90° for red color as light will experience TIR if $\beta$ is larger than 90°. If we have chosen $\beta=50°$ for the forward view design, we can read from FIG. 7(d) that at $\theta=20°$ the red ray exit angle will be about 23°, i.e. for the forward view design the FOV is (0°, 23°). If we have chosen $\beta=90°$ for the side view design, the red ray exit angle is thus 50°, i.e. the FOV is (23°, 50°). The elliptical shaded area here shows the TIR region when the incident angle is too large.

Figures 7A, 7B, 7C, 7D, 7E, 7F, 7G, 7H:
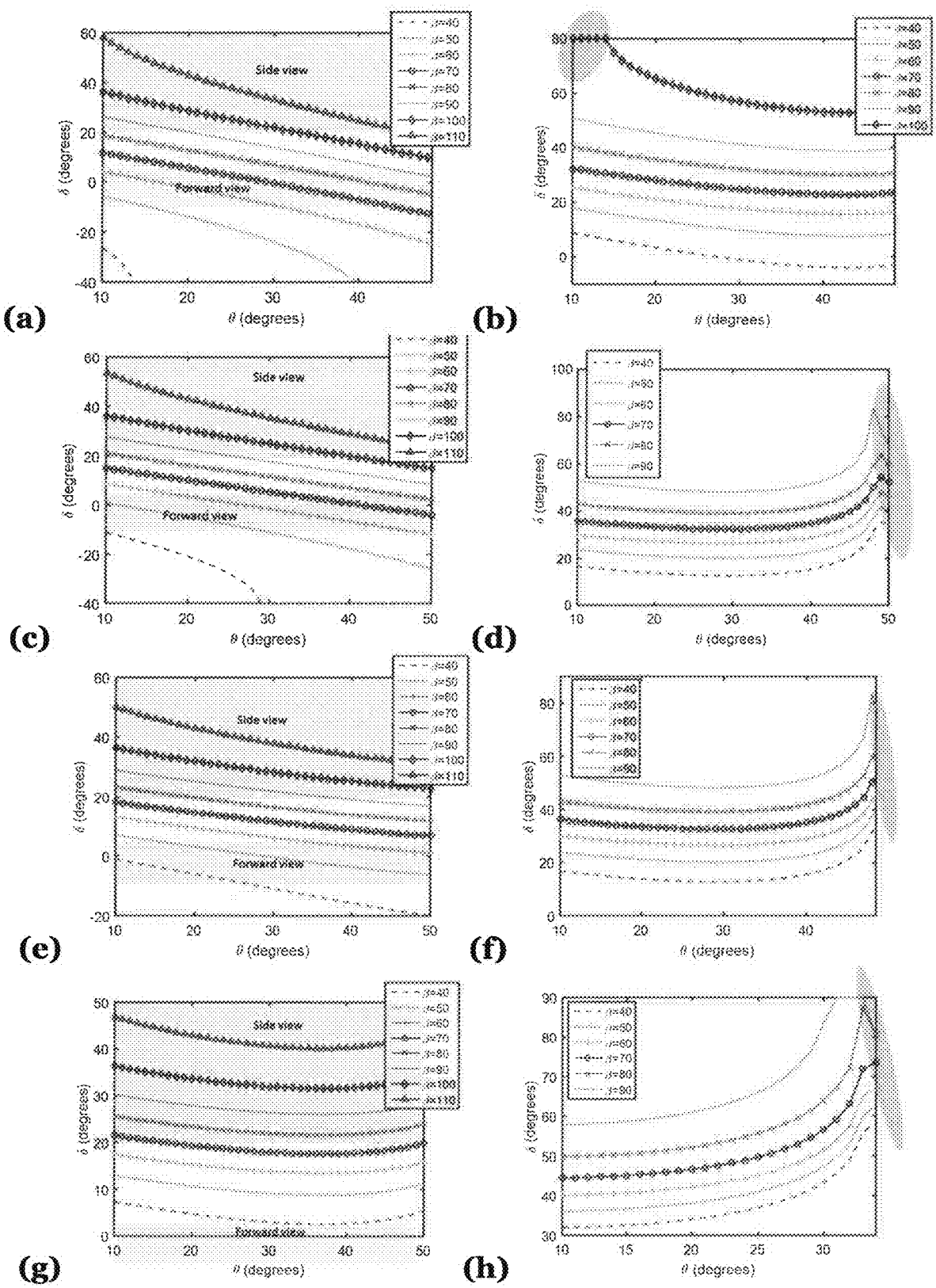
FIGS. 7(a)-7(h) are diagrams for an exemplary embodiment where the red and blue ray exit angles δ vary as a function of prism angle β and grating angle θ. $n_1=n_3=1$, G=1/0.82, λ=0.45 (blue rays) or λ=0.7 (red rays) and m=1.

We have studied similar relationships for different refractive indexes of the prism. If the refractive index of the prism $n_2=1.5$ (plastics such as PMMA), the corresponding blue ray exit angle and red ray exit angle are shown in FIGS. 7(e)-7(f). It appears that if the grating design is unchanged, a lower refractive index of the prism will shift up all the curves shown in FIG. 7(c). As a result, the usable areas for forward view design decreases and the usable area for side view design increases. A low refractive index is usually not desired as the diffraction efficiency of the grating will be lower in general.

If the refractive index of the prism $n_2=1.4$ (e.g. silicone), the corresponding blue ray exit angle and red ray exit angle are shown in FIGS. 7(g)-7(h). Again, it appears that if the grating design is unchanged, a lower refractive index of the prism will shift up all the curves shown in FIG. 7(e). As a result, the usable areas for forward view design decreases and the usable area for side view design increases. According to FIG. 7(g), it will be difficult to make a forward view probe when the refractive index is very low. A low refractive index number is usually not desired as the diffraction efficiency of the grating will also be lower in general.

If we increase the refractive index of the prism $n_2$ to 1.7 (e.g. special plastics such as high refractive index silicone or glass), the corresponding blue ray exit angle and red ray exit angle are shown in FIGS. 7(a)-7(b). It appears that if the grating design is unchanged, a higher refractive index of the prism will shift all the curves down shown in FIG. 7(c). As a result, the usable area for forward view design increases and the usable area for side view design decreases. A higher refractive index is desired as the diffraction efficiency of the grating will be higher in general.

Figures 8A, 8B:
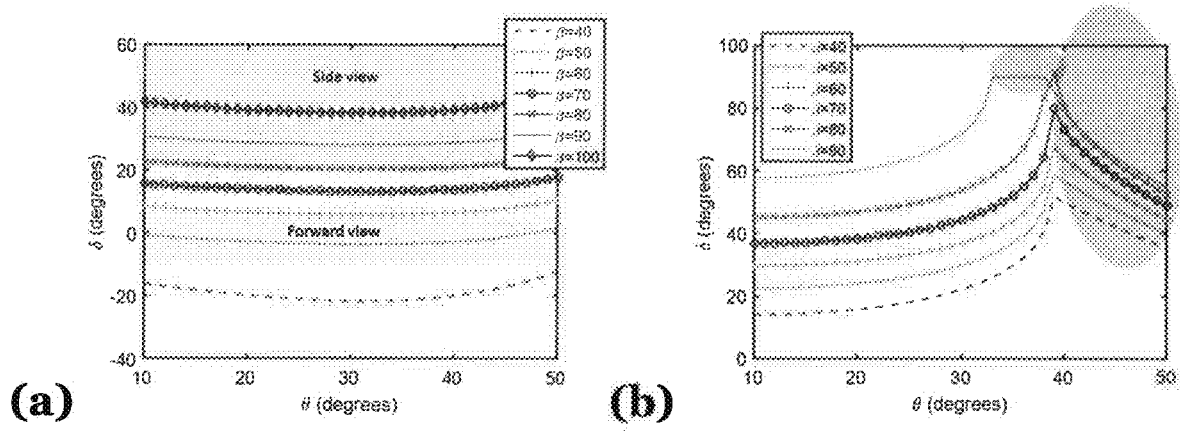
FIGS. 8(a)-8(b) are diagrams for an exemplary embodiment where the red (FIG. 8(a)) and blue (FIG. 8(b)) ray exit angles δ vary as a function of prism angle β and grating angle θ. $n_1=1.35$, $n_3=1$, $n_2=1.7$, G=1/0.82, λ=0.45 (FIG. 8(a), blue ray) or λ=0.7 (FIG. 8(b), red ray) and m=1.

Last but not least, we studied a case where the spacer is some material with lower refractive index instead of air. FIGS. 8(a)-8(b) show the case where $n_1=1.35$ and prism refractive index $n_2=1.7$. Similarly, one can find the usable ranges for both forward view design and side view design as shown in the shaded areas of FIG. 8(a). The shaded areas shown in FIG. 8(b) corresponds to TIR regions.

Methods of Fabrication

The endoscopes as described herein may be made by various techniques. For example, the focusing element 10 may be formed from a GRIN lens such as a Go!Foton or TOYO GRIN lens, supplied as cylindrical rods. The lenses are polished to desired length. TOYO GRINs were aligned and spliced to optical fiber via splicer while Go!Foton GRINs were be manually aligned with a cleaved fiber by translation stages and epoxied. The transparent element spacer was formed at the tip with epoxy and shaped by a plastic sheath or heatshrink. After curing, the transparent element was angle polished. Some designs require multiple faceted angles to the spacer. The grating was epoxy stamped to the angled surface of the transparent element.

The transparent element and grating element can also be fabricated as a single component. A plastic component with grating can be made through injection molding. A glass component can be made by etching a gating pattern on a wafer followed by machining or dicing the wafer to specifications of the spacer. A single component spacer-grating can be attached to the focusing element by epoxy after proper alignment.

Design of the detection element is also important for endoscope formation. One design can have a single detection fiber with the same angled polish and grating as the illumination optics that rotates jointly with the illumination. This design requires the detection to be part of the drive element assembly.

Another design can utilize an array of fixed detection fibers with an NA that can pick up scattered light deflected from the illumination optics. This design requires the detection array to be outside of the drive assembly. Yet another design has the detection array within a multi-lumen outer sheath. The array with sheath can be polished flat. The use of single or of multiple detection fibers may be used with the apparatus as described herein.

Sheaths may be used to protect the optics as well as provide the driving mechanism for rotation. The optics can be fixed within the drive element sheath which can be flexible (e.g., a drive cable) or rigid (e.g., a metal tube). The optics with drive element are threaded through a plastic thin walled sheath of low friction material (FEP, PTFE, PI, etc). The drive element connected to a motor will rotate the scanning optics within this sheath while the outer sheath remains stationary. The outer sheath with optics and drive element can be stand alone or be within a hand piece for handling.

A window element can be used to protect and separate the rotating optics within the sheath from everything outside of the sheath (air, liquid, bodily fluid, dust). A thin glass or plastic window is fixed with epoxy to the distal tip of the outer sheath. The window can cover the whole face of the outer sheath or just the central lumen covering solely the illumination optics and drive assembly.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

As used herein, in reference to an "inclined" surface, means that the surface of that element is not, within fabrication error, either parallel or perpendicular to the optical axis of the apparatus. For example, an inclined grating element/inclined proximal surface and an inclined distal surface will be angled by at least 5° but less than 85° (or at least 95° but less than 175°) with respect to the optical axis of the endoscope. As used herein, in reference to an "angled" surface, means that the surface of that element is not, within fabrication error, parallel to the optical axis of the apparatus. In some embodiments the grating element is angled by at least 45° but less than 80° (or at least 100° but less than 135°). In some embodiments, the angle of the grating element and the angle of the distal surface of the transparent element are inclined at different angles from each other. In some embodiments, both the grating element and the distal surface of the transparent element will be inclined with respect to the optical axis.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. An apparatus comprising:
   a light focusing element configured to focus a light along the optical axis of the apparatus,
   a grating element that is inclined with respect to the optical axis of the apparatus,
   a spacer element with a refractive index $\eta_1$ located between the light focusing element and the grating element, and
   a transparent element with a refractive index of $\eta_2$ and having a proximal surface in contact with the grating element and a distal surface that is angled with respect to the optical axis of the apparatus,
   wherein $\eta_1$ is less $\eta_2$, and
   wherein a light passing through the light focusing element enters the spacer element with the refractive index $\eta_1$ before it is incident on the grating element and wherein a light diffracting from the grating element is refracted by the distal surface of the transparent element.

2. The apparatus of claim 1, wherein the grating element and the transparent element form a single molded component.

3. The apparatus of claim 1, wherein the spacer element is an air gap.

4. The apparatus of claim 1, wherein the spacer element is an epoxy spacer.

5. The apparatus of claim 1, wherein the transparent element is a prism.

6. The apparatus of claim 1, further comprising a sheath element covering at least a portion of the apparatus wherein the grating element is not exposed outside the apparatus.

7. The apparatus of claim 1, wherein the grating element pitch is more than 600 nm.

8. The apparatus of claim 1, wherein the distal surface is angled at between 40° and 80° from the optical axis of the apparatus.

9. The apparatus of claim 1, wherein the light focusing element is a gradient index (GRIN) lens.

10. The apparatus of claim 1, wherein the light focusing element is a ball lens.

11. The apparatus of claim 1, wherein the grating element and the transparent element are made of plastic or glass and are formed through stamping, injection molding or precision molding.

12. The apparatus of claim 1, further comprising a waveguide configured to guide a light into the light focusing element.

13. The apparatus of claim 12, wherein the waveguide is attached to the light focusing element where the location of attachments is off-center from the light focusing element.

14. The apparatus of claim 12, further comprising a data generation element configured to receive and process light received from the apparatus.

15. A side-view endoscope comprising:
   a waveguide configured to guide light through the side-view endoscope,
   a light focusing element configured to focus light from the waveguide along the optical axis of the endoscope,
   a grating element that is inclined at an angle of between 40° and 80° from the optical axis of the endoscope,
   a spacer element with a refractive index $\eta_1$ located between the light focusing element and the grating element, and
   a transparent element with a refractive index of $\eta_2$ and having a proximal surface in contact with the grating element and a distal surface inclined at an angle, β, from 75° to 120°, from the optical axis of the endoscope,
   wherein $\eta_1$ is less $\eta_2$, and
   wherein a light passing through the light focusing element enters the spacer element with the refractive index $\eta_1$ before it is incident on the grating element and wherein a light diffracting from the grating element is refracted by the distal surface of the transparent element and directed at a range of angles, the lowest angle being larger than 20° with respect to the optical axis of the endoscope.

16. A forward-view endoscope comprising:
   a waveguide configured to guide light through the forward-view endoscope,
   a light focusing element configured to focus light from the waveguide along the optical axis of the apparatus,
   a grating element that is inclined an angle of between 40° and 80° from the optical axis of the endoscope,
   a spacer element with a refractive index $\eta_1$ located between the light focusing element and the grating element, and
   a transparent element with a refractive index of $\eta_2$ and having a proximal surface in contact with the grating element and a distal surface inclined at an angle, β, from 40° to 75°, with respect to the optical axis of the endoscope,
   wherein $\eta_1$ is less $\eta_2$, and
   wherein a light passing through the light focusing element enters the spacer element with the refractive index $\eta_1$ before it is incident on the grating element and wherein a light diffracting from the grating element is refracted by the distal surface of the transparent element and directed at a range of angles, the lowest angle being −10° and 5° with respect to the optical axis of the endoscope.

* * * * *